US012690873B2

(12) United States Patent
Miyamoto et al.

(10) Patent No.: US 12,690,873 B2
(45) Date of Patent: Jul. 28, 2026

(54) ANCHOR DEVICE

(71) Applicant: KOEDA Inc., Miyagi (JP)

(72) Inventors: Koichiro Miyamoto, Miyagi (JP); Toru Okuzono, Miyagi (JP)

(73) Assignee: KOEDA Inc., Miyagi (JP)

( * ) Notice: Subject to any disclaimer, the term of this patent is extended or adjusted under 35 U.S.C. 154(b) by 1079 days.

(21) Appl. No.: 17/441,557

(22) PCT Filed: Mar. 19, 2020

(86) PCT No.: PCT/JP2020/012490
§ 371 (c)(1),
(2) Date: Sep. 21, 2021

(87) PCT Pub. No.: WO2020/196336
PCT Pub. Date: Oct. 1, 2020

(65) Prior Publication Data
US 2022/0167991 A1     Jun. 2, 2022

(30) Foreign Application Priority Data

Mar. 22, 2019     (JP) ................................. 2019-054027

(51) Int. Cl.
*A61B 17/128* (2006.01)
*A61B 17/11* (2006.01)
(Continued)

(52) U.S. Cl.
CPC ...... *A61B 17/1285* (2013.01); *A61B 17/1114* (2013.01); *A61B 17/1227* (2013.01);
(Continued)

(58) Field of Classification Search
CPC .......... A61B 2017/00606; A61B 2017/00575; A61B 2017/00579; A61B 2017/00584;
(Continued)

(56) References Cited

U.S. PATENT DOCUMENTS 6,231,561 B1 * 5/2001 Frazier ............... A61B 17/0401
604/500
2007/0073337 A1 * 3/2007 Abbott ............... A61B 17/0057
606/213
(Continued)

FOREIGN PATENT DOCUMENTS

JP     2003-509175     3/2003
JP     2004-533294     11/2004
(Continued)

OTHER PUBLICATIONS

International Search Report issued Jun. 16, 2020 in International (PCT) Application No. PCT/JP2020/012490.
(Continued)

*Primary Examiner* — Thomas McEvoy
(74) *Attorney, Agent, or Firm* — Wenderoth, Lind & Ponack, L.L.P.

(57) ABSTRACT

An anchor device configured to connect a plurality of tissues to each other, includes a shaft having a longitudinal axis; and a first anchor part and a second anchor part which are separated from each other and which are each formed in the shaft. The first anchor part includes a plurality of elongated anchor arms that are allowed to be expanded in a direction of separating from the longitudinal axis of the shaft toward the second anchor part with a first position of the shaft being a base point. The second anchor part includes a plurality of elongated anchor arms that are allowed to be expanded in a direction of separating from the longitudinal axis of the shaft toward the first anchor part with a second position of the shaft being a base point.

10 Claims, 8 Drawing Sheets

(51) Int. Cl.

| | | |
|---|---|---|
| *A61B 17/122* | (2006.01) | |
| *A61B 90/00* | (2016.01) | |
| *A61B 17/00* | (2006.01) | |
| *A61B 17/064* | (2006.01) | |

(52) U.S. Cl.
CPC .... *A61B 90/37* (2016.02); *A61B 2017/00004* (2013.01); *A61B 2017/0034* (2013.01); *A61B 2017/00818* (2013.01); *A61B 2017/00867* (2013.01); *A61B 2017/0641* (2013.01); *A61B 2017/0647* (2013.01); *A61B 2017/1139* (2013.01); *A61B 2090/3784* (2016.02)

(58) Field of Classification Search
CPC ........... A61B 2017/00615; A61B 2017/00619; A61B 2017/00628; A61B 2017/081; A61B 17/08; A61B 2017/1132; A61B 2017/1135; A61B 2017/1139
See application file for complete search history.

(56) References Cited

U.S. PATENT DOCUMENTS

| | | | |
|---|---|---|---|
| 2007/0088390 A1 | 4/2007 | Paz et al. | |
| 2007/0185530 A1* | 8/2007 | Chin-Chen | ............ A61B 17/08 |
| | | | 606/213 |
| 2007/0265656 A1* | 11/2007 | Amplatz | .......... A61B 17/12122 |
| | | | 606/200 |

| | | | |
|---|---|---|---|
| 2008/0228199 A1 | 9/2008 | Cropper et al. | |
| 2009/0054913 A1 | 2/2009 | Feussner et al. | |
| 2009/0216265 A1 | 8/2009 | DeVries et al. | |
| 2010/0069955 A1 | 3/2010 | Kochman et al. | |
| 2014/0039548 A1 | 2/2014 | Whitman et al. | |
| 2018/0021044 A1 | 1/2018 | Miller et al. | |
| 2018/0042607 A1 | 2/2018 | Miller et al. | |

FOREIGN PATENT DOCUMENTS

| | | |
|---|---|---|
| JP | 4456482 | 4/2010 |
| JP | 4767292 | 9/2011 |
| JP | 2015-528732 | 10/2015 |
| WO | 99/38454 | 8/1999 |
| WO | 01/21247 | 3/2001 |
| WO | 02/087481 | 11/2002 |
| WO | 2004/019787 | 3/2004 |
| WO | 2014/025825 | 2/2014 |

OTHER PUBLICATIONS

Mori, Yasuhisa et al., "Tokyo Guidelines 2018: management strategies for gallbladder drainage in patients with acute cholecy stitus (with videos", Journal of Hepatobiliary Pancreatic Sciences, vol. 25, 2018, pp. 87-95.

Extended European Search Report dated Nov. 4, 2022 in corresponding European Patent Application No. 20777739.2.

\* cited by examiner

ANCHOR DEVICE

TECHNICAL FIELD

The present invention relates to an anchor device configured to connect a plurality of tissues to each other.

BACKGROUND ART

Cholecystitis is a disease that causes inflammation in the gallbladder. Cholecystitis is classified into acute cholecystitis and chronic cholecystitis, and the number of cases in Japan is about 100,000 per year.

As conventional therapeutic methods for cholecystitis, there are mainly given laparoscopic cholecystectomy, percutaneous transhepatic gallbladder drainage, and gallbladder-duodenum bypass surgery. The laparoscopic cholecystectomy completes medical treatment through surgical excision of the gallbladder. However, the laparoscopic cholecystectomy is highly invasive and may cause intraoperative and postoperative complications. Accordingly, the patients to whom laparoscopic cholecystectomy can be applied are limited. The percutaneous transhepatic gallbladder drainage (PTGBD) is treatment involving indwelling a drainage tube in the gallbladder via the liver to drain bile that is stagnant in the gallbladder in a certain period of time. The percutaneous transhepatic gallbladder drainage can be applied also to elderly people, emergency patients, and high-risk patients, but there are problems in that the treatment is painful and the tube is blocked or pulled out.

The gallbladder-duodenum bypass surgery is a method involving bypassing the duodenum and the gallbladder with a gastrointestinal endoscope to remove pus and gallstones. As compared to the percutaneous transhepatic gallbladder drainage, the gallbladder-duodenum bypass surgery has advantages in that the gallbladder-duodenum bypass surgery is minimally invasive, has a shorter treatment time, and has a wider applicable range. However, the gallbladder-duodenum bypass surgery is performed under a free state of walls in which holes for bypassing the duodenum and the gallbladder are formed while the gallbladder and the duodenum are not fixed to each other, and hence there is a problem in that bile may leak from a portion perforated during an operation.

As conservative treatment other than the PTGBD, there is endoscopic ultrasound-guided gallbladder drainage (EUS-GBD). In recent year, there have been found a few reports showing the effectiveness of the EUS-GBD. The EUS-GBD has the advantages in that treatment can be performed only with intravenous anesthesia without requiring general anesthesia as in cholecystectomy, there is less pain in a patient as compared to the PTGBD, there is no self-extraction by the patient, and the like. The EUS-GBD is described as a medical treatment option of Tokyo Guideline 2018 (TG18) (Non Patent Literature 1). However, the EUS-GBD is also performed under a free state in which a gallbladder wall and a gastric wall or the duodenum are not fixed to each other. Accordingly, the skill of a doctor is required, and there is a problem in that accidental symptoms caused dislocation of a stent and leakage of bile are recognized.

As a device configured to fix two tissues, in Patent Literature 1. There is disclosed a device to be used for closing a septal defect. The device includes: an inner portion having a longitudinal axis; first and second sets of fingers which are formed integrally with the inner portion, the fingers being capable of extending substantially radially from the axis, the first set of fingers not being connected to the second set of fingers in an end portion on a and radially outer side, the first and second sets being separated from each other on the axis and located apart by a distance of the axis; and a web covering only the first sets of fingers or the second sets of fingers.

In Patent Literature 2, there is disclosed a tissue locking tool to be used for connecting a plurality of tissue layers to each other. The tissue locking tool includes: a proximal end member which is configured to unfold from a delivery state to an expanded state and which includes a fixing member; a distal end member configured to unfold from a delivery state to an expanded state; and a coupling member configured to couple the proximal end member to the distal end member, to thereby apply a tensile force between the proximal end member and the distal end member. An end portion of the tissue locking tool is coupled to the coupling member and extends toward a proximal end side of the proximal end member to adjust the length of the coupling member when pulled toward the proximal end side. The fixing member is configured to be engaged with an outer surface of the coupling member, to thereby removably attach the proximal end member to the coupling member. In the expanded state, the distal end member and the proximal end member lock the plurality of tissue layers.

In Patent Literature 3, there is disclosed an anchor including a base portion and a plurality of shape-memory anchor arms. The base portion has a substantially tubular shape. The base portion is configured to define a lumen having a center line and includes an anchoring portion. The plurality of shape-memory anchor arms are coupled to the base portion so as to be substantially parallel to a central axis of the base portion. Each of the plurality of shape-memory anchor arms includes a shaft portion configured to rotate outward at the time of indwelling and a tissue penetration point coupled to be supported by the shaft portion. Each of the shaft portions is configured to rotate outward from the central axis of the base portion at the time of indwelling.

CITATION LIST

Patent Literature

[PTL 1] JP 4767292
[PTL 2] JP 4456482
[PTL 3] JP 2015-528732 A

Non Patent Literature

[NPL 1] Journal of hepato-biliary-pancreatic sciences. 2018; 25(1):87-95

SUMMARY OF INVENTION

Technical Problem

However, in any of the devices of the Literatures 1 to 3, when a plurality of fingers or anchor arms configured to fix tissues are formed integrally with a device main body, the plurality of fingers or anchor arms are formed by cutting both ends of the device main body. When tissues are perforated, distal ends of the plurality of fingers or anchor arms are brought into contact with each other, and hence there is a problem, for example, in that perforated surfaces of the tissues become rough. There is a demand for an anchor device having a different configuration that can connect a plurality of tissues to each other.

An object to be achieved by the present invention is to provide an anchor device that can connect a plurality of tissues to each other rapidly in a minimally invasive manner.

Solution to Problem

According to one mode of the present invention, there provided an anchor device configured to connect a plurality of tissues to each other, including: a shaft having a longitudinal axis; and a first anchor part and a second anchor part which are separated from each other and which are each formed in the shaft, wherein the first anchor part includes a plurality of elongated anchor arms that are allowed to be expanded in a direction of separating from the longitudinal axis of the shaft toward the second anchor part with a first position of the shaft being a base point, and wherein the second anchor part includes a plurality of elongated anchor arms that are allowed to be expanded in a direction of separating from the longitudinal axis of the shaft toward the first anchor part with a second position of the shaft being a base point.

According to another mode of the present invention, there is provided an anchor device configured to connect a plurality of tissues to each other, including: an inner shaft having a longitudinal axis; a first outer member and a second outer member which are separated from each other and which are each mounted on an outer peripheral surface of the inner shaft; and a first anchor part and a second anchor part which are formed in the first outer member and the second outer member, respectively, wherein the first anchor part includes a plurality of elongated anchor arms that are allowed to be expanded in a direction of separating from the longitudinal axis of the first outer member toward the second anchor part, and wherein the second anchor part includes a plurality of elongated anchor arms that are allowed to be expanded in a direction of separating from the longitudinal axis of the second outer member toward the first anchor part.

DESCRIPTION OF EMBODIMENTS

Now, anchor devices according to embodiments of the present invention are described with reference to FIG. 1 to FIG. 4.

First, an anchor device according to a first embodiment of the present invention is described.

Figures 1A, 1B:
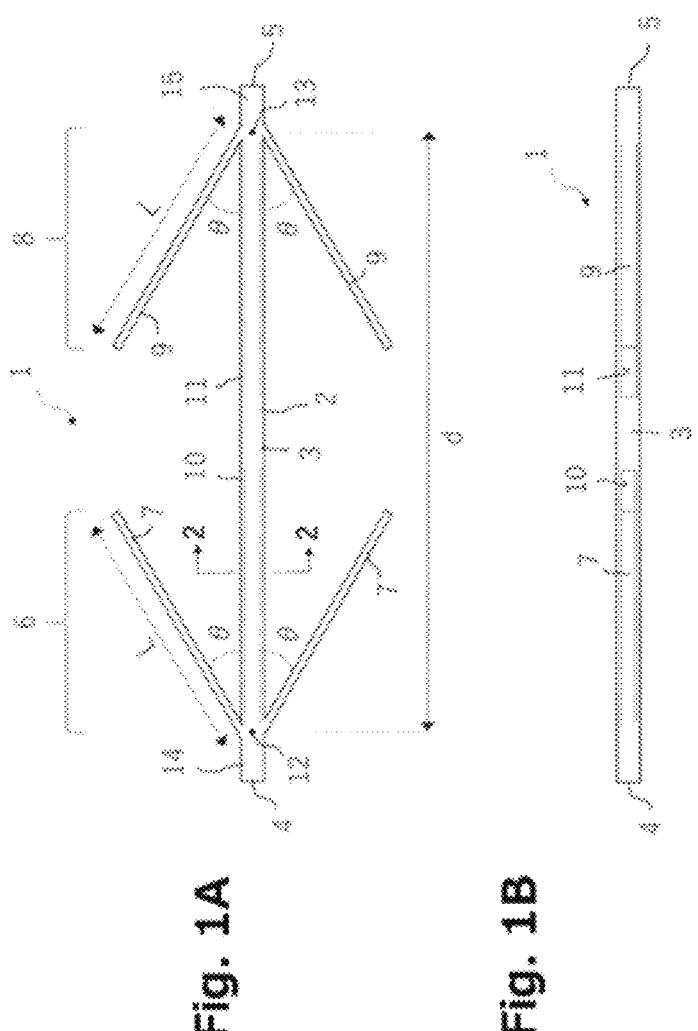
FIG. 1A is a side view of an anchor device according to a first embodiment of the present invention.
FIG. 1B is a plan view of the anchor device.

As illustrated in FIG. 1A, an anchor device 1 configured to connect a plurality of tissues to each other includes an elongated shaft 2 having a longitudinal axis, and a first anchor part 6 and a second anchor part 8 which are separated from each other and which are each formed in the shaft 2. The first anchor part 6 includes a plurality of elongated anchor arms 7, and the second anchor part 8 includes a plurality of elongated anchor arms 9. Connecting the plurality of tissues to each other refers to that the plurality of tissues are held in contact with each other between the first anchor part and the second anchor part of the anchor device of the present invention.

The plurality of elongated anchor arms 7 of the first anchor part 6 are formed of portions obtained by cutting out the shaft 2 between a first position 12 and a second position 13 along a longitudinal direction of the shaft 2 and form a part of the shaft 2. In addition, the plurality of elongated anchor arms 9 of the second anchor part 8 are also formed of portions obtained by cutting out the shaft 2 between the first position 12 and the second position 13 along the longitudinal direction of the shaft 2 and form a part of the shaft 2. It is preferred that a distance "d" between the first position 12 and the second a position 13 and a length L of each of the elongated anchor arms 7 and 9 satisfy $2L \leq d$.

A diameter of the shaft 2, a total length of the shaft, the distance "d", and the length L of each of the elongated anchor arms 7 and 9 may vary depending on the place of use, and are not particularly limited. For example, the total length of the shaft may be set to from 10 mm to 50 mm, the distance "d" may be set to from 8 mm to 45 mm, and the length L of each of the elongated anchor arms 7 and 9 may be set to from 1 mm to 20 mm.

The first position 12 and the second position 13 of the shaft 2 are separated from a first end 4 and a second end 5 of the shaft 2. That is, a first end portion 14 having a certain length is present between the first end 4 and the first position 12 of the shaft 2, and a second end portion 15 having a certain length is present between the second end 5 and the second position 13 of the shaft 2.

The plurality of elongated anchor arms 7 of the first anchor part 6 are allowed to be expanded in a direction of separating from the longitudinal axis of the shaft 2 toward the second anchor part 8 with the first position 12 in a longitudinal direction of a shaft main body 3 extending in the longitudinal direction of the shaft 2 being a base point. In addition, the plurality of elongated anchor arms 9 of the second anchor part 6 are allowed to be expanded in a direction of separating from the longitudinal axis of the shaft 2 toward the first anchor part 6 with the second anchor position 13 extending in the longitudinal direction of the shaft 2 being a base point.

Accordingly, as is understood in FIG. 1B, when the shaft 2 has an expanded configuration, that is, when the plurality of elongated anchor arms 7 of the first anchor part 6 and the plurality of elongated anchor arms 9 of the second anchor part 8 are respectively expanded, and the plurality of elongated anchor arms 7 and 9 stand up from the shaft main body 3 extending in the longitudinal direction of the shaft 2, the shaft 2 has cutout holes 10 and 11.

The material of the shaft 2 is not particularly limited, and there may be used, for example, a metal, a metal alloy, a thermoplastic plastic, a biodegradable resin, or any other medical grade material.

Examples of the metal include, but not limited to, stainless steel, gold, platinum, titanium, and tantalum.

Examples of the metal alloy include, but not limited to, a nickel titanium alloy (nitinol), an iron-manganese-silicon alloy, and a cobalt chromium alloy.

Examples of the thermoplastic plastic include, but not limited to, polymethyl methacrylate, polymethyl acrylate, polystyrene, acrylonitrile butadiene styrene, polyvinyl chloride, modified polyethylene terephthalate glycol, cellulose acetate butyrate, polyethylene, high-density polyethylene, low-density polyethylene, polypropylene, polymethylpentene, polycarbonate, polyphenylene oxide, polyphenylene ether, thermoplastic polyurethane, polyamide, polyoxymethylene, polyethylene terephthalate, polybutylene terephthalate, ultrahigh-molecular-weight polyethylene, polyimide, polyamide imide, polybenzimidazole, polysulfone, polyetherimide, polyethersulfone, polyarylsulfone, polyphenylene sulfide, polyether ether ketone, fluoropolymers (e.g., fluorinated ethylene propylene, ethylene chlorotrifluoroethylene, ethylene tetrafluoroethylene, polychlorotrifluoroethylene, and polytetrafluoroethylene), polyvinylidene fluoride, and perfluoroalkoxy.

Examples of the biodegradable resin include, but not limited to, L form and D form polylactic acids (PLA), polyglycolic acid (PGA), a copolymer of polylactic acid and polyglycolic acid (PLGA), polycaprolactone (PCL), DL-lactide-co-ε-caprolactone (DL-PLCL), poly(4-hydroxy butyrate) (P4HB), poly(valerolactone), polydioxanone, polybutylene adipate terephthalate, poly(ethylene terephthalate), and cellulose acetate (CDA).

Examples of the other medical grade material include, but not limited to, an organosilicon elastomer polymer, polyether block amide, and a thermoplastic copolyether (PEBAX).

From the viewpoint of using a highly elastic material, the material for the shaft 2 is preferably a nickel-titanium alloy (Nitinol) or a thermoplastic plastic. From the viewpoint of high rigidity or compression resistance, the material for the shaft 2 is preferably a nickel-titanium alloy or stainless steel. From the viewpoint of shape memory, a nickel-titanium alloy is preferred.

The shaft 2 is preferably a self-expandable shaft that has an expanded configuration under a state in which no external pressure is applied (also referred to as "released state" or "free state"). The self-expandable shaft may be manufactured through use of Nitinol or the like. When the shaft 2 is formed of a self-expandable shaft, the anchor device 1 according to the first embodiment can be used as a self-expandable anchor device that can be expanded by itself.

An angle θ at which the plurality of elongated anchor arms 7 of the first anchor part 6 and the plurality of elongated anchor arms 9 of the second anchor part 8 can be expanded with respect to the longitudinal axis of the shaft 2 is preferably 90° at maximum, more preferably 75° at maximum, still more preferably 45° at maximum. When the angle θ is larger, the first anchor part 6 or the second anchor part 7 of the anchor device 1 can be satisfactorily maintained without returning to be pulled out after passing through the tissues. However, when the angle θ is smaller, after the first anchor part 6 or the second anchor part 7 of the anchor device 1 passes through the tissues, damage to the tissues when the anchor device 1 is withdrawn from the tissues can be reduced.

Figure 2:
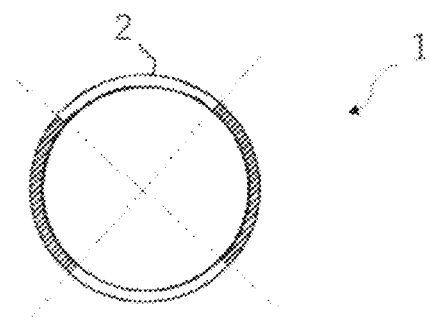
FIG. 2 is a sectional view of the anchor device taken along the line 2-2 of FIG. 1A.

The shaft 2 of the anchor device 1 according to the first embodiment includes the two anchor parts 6 and 8, and as illustrated in FIG. 2, the length of one arc obtained by equally dividing a substantially circular hollow cross-section into four parts corresponds to a length in a circumferential direction of each of the anchor parts 6 and 8.

The anchor device 1 can assume a contracted state in which the plurality of elongated anchor arms 7 of the first anchor part 6 and the plurality of elongated anchor arms 9 of the second anchor part 8 are substantially parallel to the longitudinal axis of the shaft 2. In the contracted state, the plurality of elongated anchor arms 7 of the first anchor part 6 and the plurality of elongated anchor arms 9 of the second anchor part 8 can form an angle of preferably from 0° to 10°, more preferably from 0° to 5°, still more preferably 0° with respect to the longitudinal axis of the shaft 2.

Figure 3:
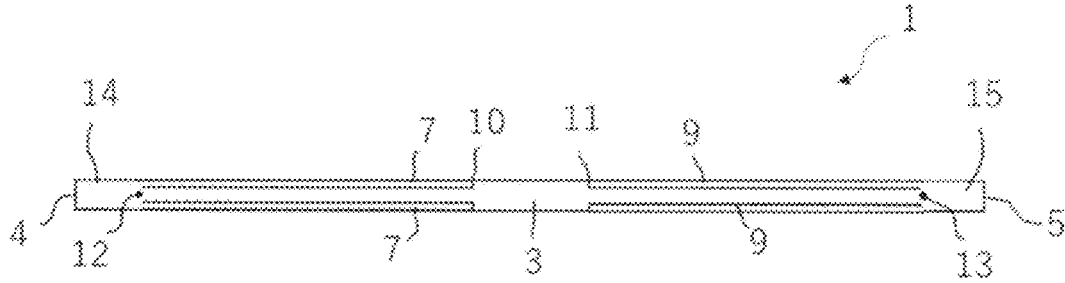
FIG. 3 is a side view of the anchor device of FIG. 1 in a contracted state.

In the case in which the shaft 2 is a self-expandable shaft, when the pressure applied to the anchor device 1 is increased, the angle formed by the elongated anchor arms 7 and 9 with respect to the longitudinal axis of the shaft 2 becomes smaller. In a case in which sufficient pressure is applied to the shaft 2, as illustrated in FIG. 3, in the shaft 2 of the anchor device 1 according to the first embodiment, the plurality of elongated anchor arms 7 of the first anchor part 6 and the plurality of elongated anchor arms 9 of the second anchor part 8 can be placed at positions along the longitudinal axis of the shaft 2 when external pressure is applied. This is a state in which each of the elongated anchor arms 7 and 9 forms an angle of 0° with respect to the longitudinal axis of the shaft 2 and the closed anchor arms 7 and 9 are accommodated in the cutout holes 10 and 11.

The anchor device 1 according to the first embodiment may be manufactured by producing the shaft 2 from a publicly known material, such as a metal, a metal alloy, a thermoplastic plastic, a biodegradable resin, and other medical grade materials, and cutting portions on the shaft 2 in which the first anchor part 6 and the second anchor part 8 are to be formed with cutting means, such as a publicly known laser processing device.

Next, an example of treatment for connecting two tissues to each other through use of the anchor device 1 according to the first embodiment of the present invention is described with reference to FIG. 4A to FIG. 4C. There is given an example in which a gallbladder wall and a duodenal wall are caused to adhere to each other with the anchor device 1.

Figure 4A:
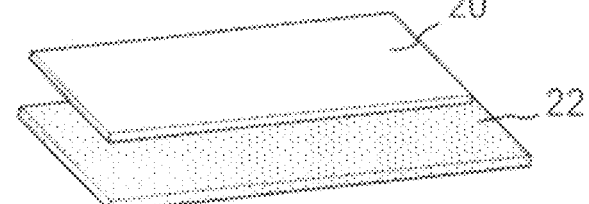
FIG. 4A, FIG. 4B, and FIG. 4C are each a schematic view for illustrating adhesion between two tissues through use of the anchor device.
Figure 4B:
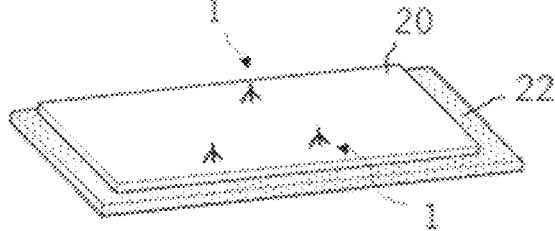
Figure 4C:
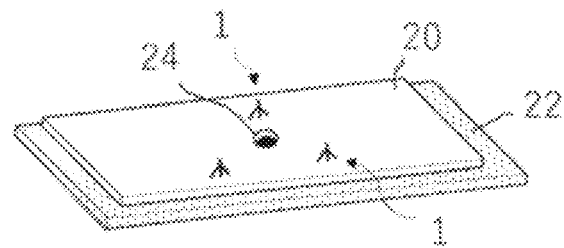

In FIG. 4A, a gallbladder wall 20 and a duodenal wall 22 are illustrated. As illustrated in FIG. 4B, the anchor device 1 penetrates through the duodenal wall 22 and the gallbladder wall 20 to connect the duodenal wall 22 and the gallbladder wall 20 to each other under a state in which the anchor device 1 itself is expanded. A plurality of locations (three locations in the figure) of the gallbladder wall 20 and the duodenal wall 22 are connected and fixed to each other with the anchor device 1, and then a fistula 24 is formed as illustrated in FIG. 4C. In this state, bile is drained from the gallbladder into the duodenum. According to this configuration, the operation of opening the fistula 24 is performed under a state in which the gallbladder wall 20 and the duodenal wall 22 are fixed to each other, and hence the operation of forming the fistula becomes easier. In addition, the leakage of the bile from a location in which the fistula 24 is formed can be suppressed or eliminated.

Next, an example of a procedure for connecting two tissues to each other through use of the anchor device 1 according to the first embodiment of the present invention is described in more detail with reference to FIG. 5A to FIG. 5E. In FIG. 5B to FIG. 5E, an ultrasonic endoscope 25 is omitted in order to clearly illustrate the operation of the anchor device 1 and an endoscopic ultrasound-guided needle tube 26.

Figures 5A, 5B, 5C, 5D, 5E:
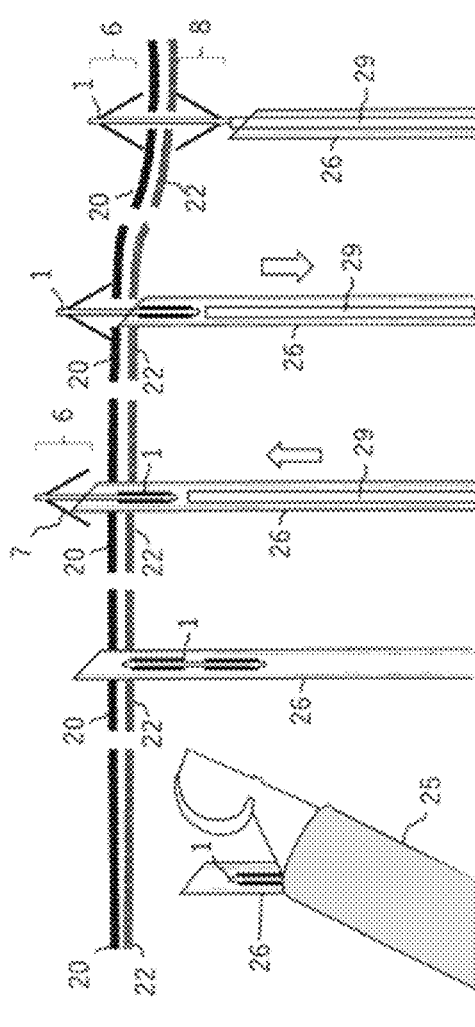
FIG. 5A, FIG. 5B, FIG. 5C, FIG. 5D, and FIG. 5E are schematic views for illustrating a procedure for connecting the two tissues to each other through use of the anchor device of FIG. 1.

First, a doctor inserts the ultrasonic endoscope 25 into a gastrointestinal tract through the mouth of a patient and advances the ultrasonic endoscope 25 in the gastrointestinal tract while observing with a monitor (FIG. 5A). The gallbladder is visualized from the duodenal wall with the ultrasonic endoscope 25. The needle tube 26 of an endoscopic ultrasound guided puncture needle is inserted into a forceps channel in the ultrasonic endoscope 25, and the needle tube 26 is caused to penetrate through the duodenal wall 22 and the gallbladder wall 20 (FIG. 5B). After a distal end of the needle tube 26 passes through the gallbladder wall 20, an extrusion member, such as a stylet 29, is advanced from a proximal end direction of the gastrointestinal endoscope 25 toward a distal end direction in the direction of the arrow, and the anchor device 1 is pushed out from the inside of the needle tube 26 (FIG. 5C). The first anchor part 6 of the anchor device 1 having been pushed out is autonomously expanded with elasticity or the like, and the return of the first anchor part 6 through a hole formed in the gallbladder wall 20 is regulated when the needle tube 26 is pulled back in the direction of the arrow (FIG. 5D). Next, when the needle tube 26 is further pulled back, the anchor device 1 is completely released from the needle tube 26, and the second anchor part 8 of the anchor device 1 is also autonomously expanded with elasticity or the like. Under a state in which the anchor device 1 is expanded in this manner, the gallbladder wall 20 and the duodenal wall 22 are held between the first anchor part 6 and the second anchor part 8 of the anchor device 1 and are caused to adhere to be fixed to each other (FIG. 5E). After that, the needle tube 26 is retrieved into the gastrointestinal endoscope 25, and the gastrointestinal endoscope 25 is pulled back to the outside of the body. After the procedure in FIG. 5A to FIG. 5E are repeated to fix the gallbladder wall 20 and the duodenal wall 22 at a plurality of locations, the fistula 24 is formed as illustrated in FIG. 4C, and a drainage tube is indwelled. With this, a solution in the gallbladder is drained.

When the drainage of bile from the gallbladder to the duodenum subsides, and the inflammation of the gallbladder is alleviated, with the result that the state subsides, the gastrointestinal endoscope 25 is advanced again in the gastrointestinal tract to the position of the anchor device 1. A publicly known gripping device such as forceps or a snare accommodated in the gastrointestinal endoscope 25 is advanced from the distal end of the gastrointestinal endoscope 25 to the outside to grip the second anchor part 8 of the anchor device 1. Then, the gripping device is pulled back in the proximal end direction of the gastrointestinal endoscope 25 to collect the anchor device 1 into the gastrointestinal endoscope 25.

The effects of the anchor device according to the first embodiment of the present invention are described.

(1) In the anchor device 1 according to the first embodiment, as compared to a conventional surgical operation, a plurality of tissues can be connected to each other rapidly in a minimally invasive manner, and the skill of an operator is not required. In addition, a technique such as fistula formation after connection of the plurality of tissues becomes easier.

(2) In the anchor device 1 according to the first embodiment, the first anchor part 6 and the second anchor part 8 are converged at the first position 12 and the second position 13 of the shaft 2, respectively. Accordingly, the foregoing is advantageous when the anchor device 1 according to the first embodiment is advanced in a living body (particularly in the gastrointestinal tract) or when the anchor device 1 is caused to pass through the tissues. In addition, also when the anchor device 1 is pulled out from the tissues and retrieved, the second anchor part 8 is expanded in a direction opposite to the direction in which the anchor device 1 is pulled out, and hence the collection is easy.

(3) The anchor device 1 according to the first embodiment is formed of one member such as the shaft 2. Accordingly, the configuration is simple, and the anchor device 1 can be manufactured at low cost.

The anchor device 1 according to the first embodiment of the present invention has been described above, but the anchor device 1 according to the first embodiment may be modified as follows.

The number of the elongated anchor arms 7 of the first anchor part 6 and the number of the elongated anchor arms 9 of the second anchor part 8 are not each limited to two. For example, the number of the elongated anchor arms 7 of the first anchor part 6 and the number of the elongated anchor arms 9 of the second anchor part 6 may be each three as illustrated in FIG. 6, four as illustrated in FIG. 7, or five or more.

Figure 6:
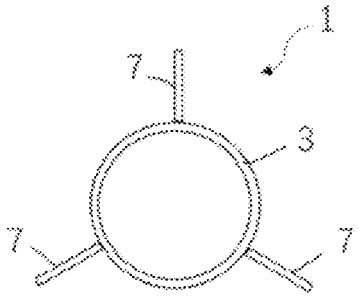
FIG. 6 is a schematic end view for illustrating another example of an anchor arm.
Figure 7:
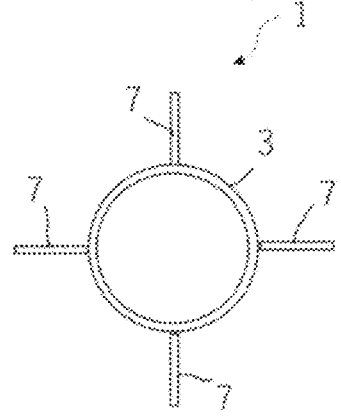
FIG. 7 is a schematic end view for illustrating another example of an anchor arm.

In the examples illustrated in FIG. 2, FIG. 6, and FIG. 7, each of the plurality of elongated anchor arms 7 of the first anchor part 6 and the plurality of elongated anchor arms 9 of the second anchor part 8 is formed so as to correspond to one arc obtained by equally dividing the cross-section of the shaft 2, but the elongated anchor arms 7 and 9 are not required to be formed at equal intervals in a circumferential direction of the shaft 2. In addition, the circumferential length of the elongated anchor arms 7 and 9 on the shaft 2 are not required to be matched with the circumferential length of a portion of the shaft 2 between the adjacent elongated anchor arms 7. The circumferential length of the elongated anchor arms 7 and 9 on the shaft 2 is not required to be matched with the circumferential length of a portion of the shaft 2 between the adjacent elongated anchor arms 9.

Figure 8:
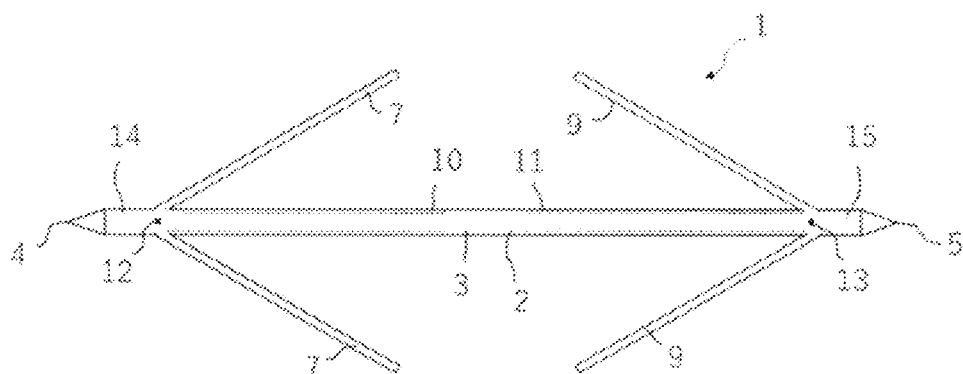
FIG. 8 is a side view for illustrating another example of an anchor device.

As illustrated in FIG. 8, the first end 4 and the second end 5 of the anchor device 1 may be sharpened. With such a configuration, the penetration of the anchor device 1 into the tissues becomes easier.

Figure 9:
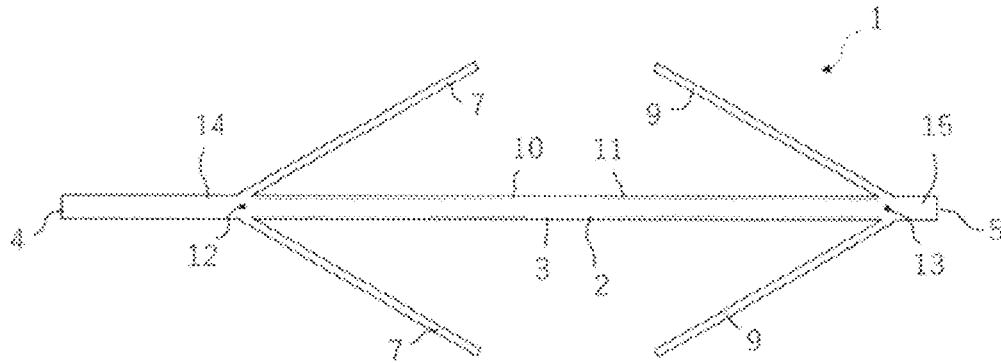
FIG. 9 is a side view for illustrating another example of an anchor device.

The anchor device 1 may be asymmetric. For example, as illustrated in FIG. 9, the length of the first end portion 14 between the first end 4 and the first position 12 of the shaft 2 may be different from the length of the second end portion 15 between the second end 5 and the second position 13 of the shaft 2. With such a configuration, one of the first end 4 and the second end 5 is defined as a distal end on a side that is caused to penetrate the tissues, and the other of the first end 4 and the second end 5 is defined as a proximal end on a side closer to the operator of the anchor device 1. Thus, one of the first end 4 and the second end 5 and the other of the first end 4 and the second end 5 can be distinguished from each other.

In the first embodiment, the elongated anchor arms 7 of the first anchor part 6 and the elongated anchor arms 9 of the second anchor part 8 have a symmetric relationship. However, the elongated anchor arms 7 of the first anchor part 6 and the elongated anchor arms 9 of the second anchor part 8 may vary in size and/or number.

Figure 10:
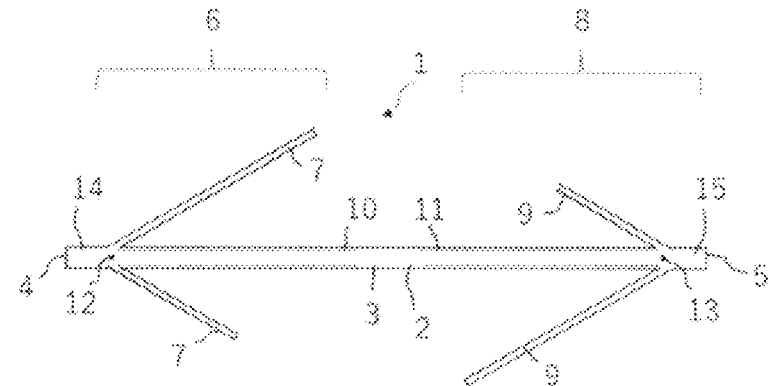
FIG. 10 is a side view for illustrating another example of an anchor device.

As illustrated in FIG. 10, the lengths of the plurality of elongated anchor arms 7 of the first anchor part 6 may be different from each other, and the lengths of the plurality of elongated anchor arms 9 of the second anchor part 8 may also be different from each other.

The plurality of elongated anchor arms 7 of the first anchor part 6 and the plurality of elongated anchor arms 9 of the second anchor part 8 are formed by cutting out the shaft 2 with cutting means such as a laser processing device. However, the forming method of the plurality of elongated anchor arms 7 and 9 is not limited.

Figure 11:
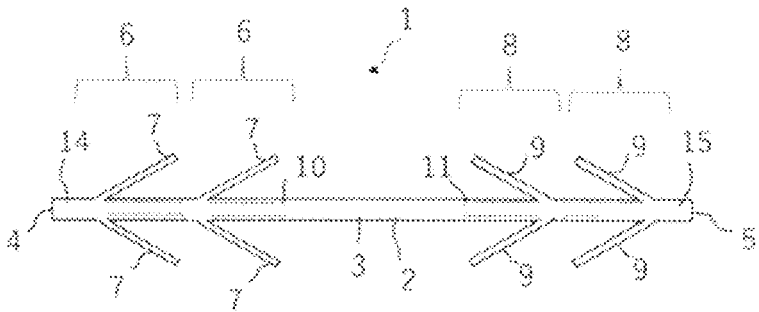
FIG. 11 is a side view for illustrating another example of an anchor device.

As illustrated in FIG. 11, a plurality of first anchor parts 6 may be formed along the shaft 2, and a plurality of second anchor parts 8 may be formed along the shaft 2.

The shaft 2 in the first embodiment is hollow, but the shaft 2 may be solid.

Under a state in which no external pressure is applied to the shaft 2, each of the plurality of elongated anchor arms 7 of the first anchor part 6 and the plurality of elongated anchor arms 9 of the second anchor part 8 forms the angle θ of 90° at maximum with respect to the longitudinal axis of the shaft 2. However, the elongated anchor arms 7 and 9 may be configured so that the elongated anchor arms 7 and 9 each move to a position at which the θ is more than 90°, preferably a position at which the θ is from 150° to 180° when external pressure is applied to the elongated anchor arms 7 and 9 from the expanded direction to the converged direction of the elongated anchor arms 7 and 9 (that is, in a direction from the second end 5 to the first end 4 in parallel the longitudinal axis of the shaft 2 with respect to the elongated anchor arms 7 in FIG. 1, and a direction from the first end 4 to the second end 5 in parallel to the longitudinal axis of the shaft 2 with respect to the elongated anchor arms 9 in FIG. 1). In this case, as illustrated in FIG. 5E, when the anchor device 1 is expanded to fix the gallbladder wall 20 and the duodenal wall 22 to each other, and then the anchor device 1 is pulled out from the tissues and retrieved, the second anchor part 8 is expanded in a direction opposite to the direction in which the anchor device 1 is pulled out, and in addition, the first anchor part 6 is also brought into abutment against the gallbladder wall 20 to be expanded in a direction opposite to the direction in which the anchor device 1 is pulled out. Accordingly, the collection of the anchor device 1 becomes easier.

The application of the anchor device 1 according to the first embodiment is not limited to gallbladder-duodenal bypass surgery. For example, the anchor device 1 according to the first embodiment may be used for connecting two tissues including hollow organs other than the duodenum, such as a hollow organ and a hollow organ, a hollow organ and a parenchymal organ, a parenchymal organ and a parenchymal organ, a mesothelium and a hollow organ, and a mesothelium and a parenchymal organ, to each other.

Next, an anchor device according to a second embodiment of the present invention is described. The description of the same members as those of the anchor device according to the first embodiment is omitted.

Figure 12:
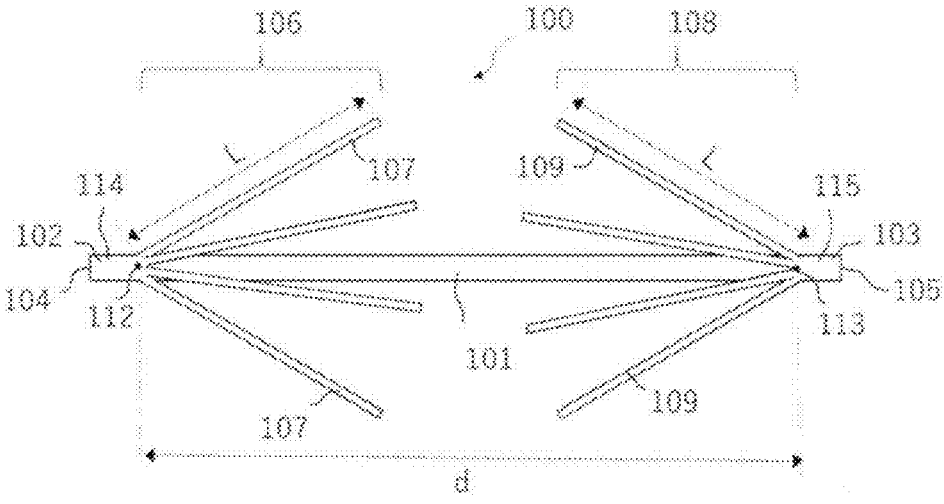
FIG. 12 is a side view of an anchor device according to a second embodiment of the present invention.
Figure 13:
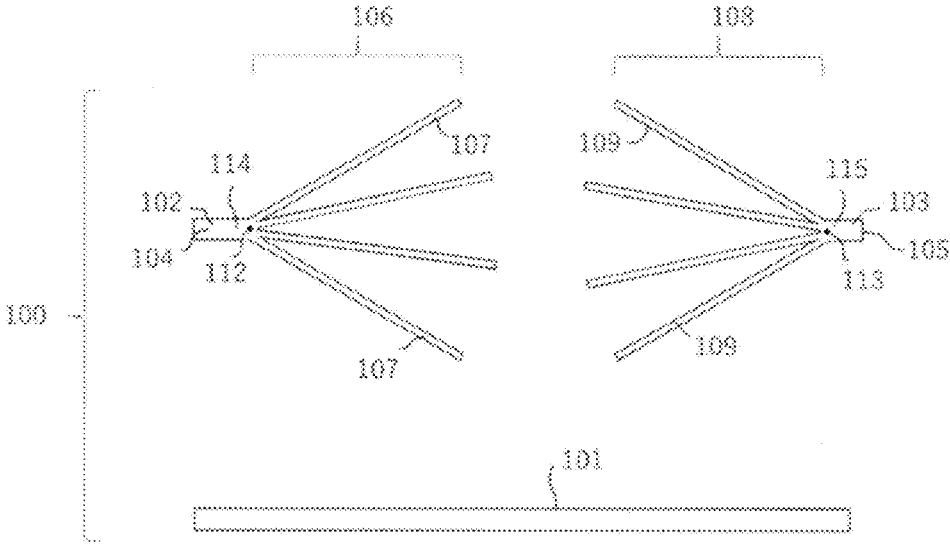
FIG. 13 is an exploded view of the anchor device of FIG. 12.

As illustrated in FIG. 12 and FIG. 13, an anchor device 100 configured to connect a plurality of tissues to each other includes: an inner shaft 101 having a longitudinal axis; a first outer shaft 102 serving as a first outer member and a second outer shaft 103 serving as a second outer member which are separated from each other and which are each mounted on an outer peripheral surface of the inner shaft 101; and a first anchor part 106 and a second anchor part 108 which are formed in the first outer shaft 102 and the second outer shaft 103, respectively. The first anchor part 106 includes a plurality of elongated anchor arms 107 that are allowed to be expanded in a direction of separating from the longitudinal axis of the first outer shaft 102 toward the second anchor part 108, and the second anchor part 108 includes a plurality of elongated anchor arms 109 that are allowed to be expanded in a direction of separating from the longitudinal axis of the second outer shaft 103 toward the first anchor part 106.

The plurality of elongated anchor arms 107 of the first anchor part 106 are formed of portions obtained by cutting out the first outer shaft 102 and form a part of the first outer shaft 102. The plurality of elongated anchor arms 109 of the second anchor part 108 are also formed of portions obtained by cutting out the second outer shaft 103 and form a part of the second outer shaft 103.

It is preferred that a distance "d" between a first position 112 of the first outer shaft 102 and a second position 113 of the second outer shaft 103 and a length L of each of the elongated anchor arms 107 and 109 satisfy 2L≤d.

Also in the anchor device 100 according to the second embodiment, the first position 112 of the outer shaft 102 and the second position 113 of the outer shaft 103 are separated from a first end 104 of the outer shaft 102 and a second end 105 of the outer shaft 103. That is, a first end portion 114 having a certain length is present between the first end 104 and the first position 112 of the outer shaft 102, and a second end portion 115 having a certain length is present between the second end 105 and the second position 113 of the outer shaft 103. Accordingly, the foregoing is advantageous when the anchor device 100 is advanced in a living body (particularly in the gastrointestinal tract) or when the anchor device 100 is caused to pass through the tissues.

A diameter of the inner shaft 101 and the outer shafts 102 and 103, a total length of the inner shaft 101, the distance "d", and the length L of each of the elongated anchor arms 107 and 109 may vary depending on the place of use, and are not particularly limited. For example, the total length of the inner shaft 101 may be set to from 10 mm to 50 mm, the distance "d" may be set to from 8 mm to 45 mm, and the length L of each of the elongated anchor arms 107 and 109 may be set to from 1 mm to 20 mm.

The plurality of elongated anchor arms 107 of the first anchor part 106 are allowed to be expanded in a direction of separating from the longitudinal axis of the shaft 102 toward the second anchor part 108 with the first position 112 in a longitudinal direction of the shaft 102 being a base point. In addition, the plurality of elongated anchor arms 109 of the second anchor part 108 are allowed to be expanded in a direction of separating from the longitudinal axis of the shaft 103 toward the first anchor part 106 with the second position 113 in the longitudinal direction of the shaft 102 being a base point.

Figure 14:
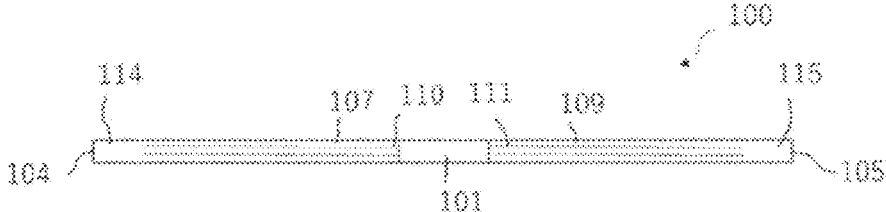
FIG. 14 is a side view of the anchor device of FIG. 12 in a contracted state.

Accordingly, as is understood in FIG. 14, when the outer shafts 102 and 103 have an expanded configuration, that is, when the plurality of elongated anchor arms 107 of the first anchor part 106 and the plurality of elongated anchor arms 109 of the second anchor part 108 are respectively expanded, and the plurality of elongated anchor arms 107 and 109 stand up from the outer shafts 102 and 103, the outer shafts 102 and 103 have cut portions 110 and 111, respectively.

The materials of the shafts 101, 102, and 103 are not particularly limited, and there may be used, for example, a metal, a metal alloy, a thermoplastic plastic, a biodegradable resin, or any other medical grade material. Such materials are as described regarding the anchor device 1 according to the first embodiment.

Each of the outer shafts 102 and 103 is preferably a self-expandable shaft that has an expanded configuration under a state in which no external pressure is applied (also referred to as "released state" or "free state"). The self-expandable shaft may be manufactured through use of Nitinol or the like. When the outer shafts 102 and 103 are each formed of a self-expandable shaft, the anchor device 100 according to the second embodiment can be used as a self-expandable anchor device that can be expanded by itself.

An angle θ at which the plurality of elongated anchor arms 107 of the first anchor part 106 and the plurality of elongated anchor arms 109 of the second anchor part 108 can be expanded with respect to the longitudinal axis of each of the outer shafts 102 and 103 is preferably 90° at maximum, more preferably 75° at maximum, still more preferably 45° at maximum. When the angle θ is larger, the first anchor part 106 or the second anchor part 107 of the anchor device 100 can be satisfactorily maintained without returning to be pulled out after passing through the tissues. However, when the angle θ is smaller, after the first anchor part 106 or the second anchor part 107 of the anchor device 100 passes through the tissues, damage to the tissues when the anchor device 100 is retrieved from the tissues can be reduced.

The outer shafts 102 and 103 of the anchor device 100 according to the second embodiment include the anchor parts 106 and 108, respectively, and the length of one arc obtained by equally dividing a substantially circular hollow cross-section into four parts corresponds to a length in a circumferential direction of each of the anchor parts 107 and 109.

The anchor device 100 can assume a contracted state in which the plurality of elongated anchor arms 107 of the first anchor part 106 and the plurality of elongated anchor arms 109 of the second anchor part 108 are substantially parallel to the longitudinal axis of each of the outer shafts 102 and 103. The plurality of elongated anchor arms 107 of the first anchor part 106 and the plurality of elongated anchor arms 109 of the second anchor part 108 can form an angle of preferably from 0° to 10°, more preferably from 0° to 5° with respect to the longitudinal axis of the inner shaft 101 and the longitudinal axis of each of the outer shafts 102 and 103, still more preferably 0° with respect to the longitudinal axis of the inner shaft 101 and the longitudinal axis of each of the outer shafts 102 and 103.

In the case in which each of the outer shafts 102 and 103 is a self-expandable shaft, when the pressure applied to the anchor device 1 is increased, the angle formed by the elongated anchor arms 107 and 109 with respect to the longitudinal axis of each of the outer shafts 102 and 103 becomes smaller. In a case in which sufficient pressure is applied to the outer shafts 102 and 103, as illustrated in FIG. 14, in the outer shafts 102 and 103 of the anchor device 100 according to the second embodiment, the plurality of elongated anchor arms 107 of the first anchor part 6 and the plurality of elongated anchor arms 109 of the second anchor part 108 can be placed at positions along the longitudinal axis of the inner shaft 101 and the longitudinal axis of each of the outer shafts 102 and 103 when external pressure is applied. This is a state in which each of the elongated anchor arms 107 and 109 forms an angle of 0° with respect to the longitudinal axis of each the shafts 102 and 103.

The anchor device 100 according to the second embodiment may be manufactured by producing the outer shafts 102 and 103 from a publicly known material, such as a metal, a metal alloy, a thermoplastic plastic, a biodegradable resin, and other medical grade materials, and cutting portions on the shaft 2 in which the first anchor part 106 and the second anchor part 108 are to be formed with cutting means, such as a publicly known. laser processing device.

Examples of treatment of connecting two tissues to each other through use of the anchor device 100 according to the second embodiment of the present invention and a procedure for connecting the two tissues to each other through use of the anchor device 100 according to the second embodiment of the present invention are as illustrated in FIG. 4 and FIG. 5.

The effects of the anchor device 100 according to the second embodiment of the present invention are described.

The anchor device 100 according to the second embodiment of the present invention has the following effects in addition to the above-mentioned effects (1) and (2) of the anchor device 1 according to the first embodiment.

(3) In addition to the above-mentioned effects (1) and (2) of the anchor device 1 according to the first embodiment of the present invention, the strength along the longitudinal axis of the anchor device 1 is increased because the anchor device 100 according to the second embodiment is formed of the inner shaft 101 and the two outer shafts 102 and 103.

(4) The elongated anchor arms 107 and 109 can be formed in the entire circumference of each of end faces of the outer shafts 102 and 103, and hence the number and areas of the anchor arms 7 and 9 can be increased as compared to the elongated anchor arms 7 and 9 in the first embodiment.

The anchor device 100 according to the second embodiment has been described above, but the anchor device 100 according to the second embodiment may be modified as follows.

The number of the plurality of elongated anchor arms 107 of the first anchor part 106 and the number of the plurality of elongated anchor arms 109 of the second anchor part 108 are not each limited as long as the number is two or more.

Each of the plurality of elongated anchor arms 107 of the first anchor part 106 and the plurality of elongated anchor arms 109 of the second anchor part 108 is formed so as to correspond to one arc obtained by equally dividing the cross-section of the first outer shaft 102 and the second outer shaft 103, but the elongated anchor arms 107 and 109 are not required to be formed at equal intervals in a circumferential direction of the shaft 2. In addition, the circumferential length of the elongated anchor arms 107 and 109 on the shafts 102 and 103 are not required to be matched with the circumferential length of a portion of the first outer shaft 102 between the adjacent elongated anchor arms 107. The circumferential length of the elongated anchor arms 107 and 109 on the shafts 102 and 103 is not required to be matched with the circumferential length of a portion of the second outer shaft 103 between the adjacent elongated anchor arms 109.

Both ends of the inner shaft 101, the end 104 of the first outer shaft 102, and the end 105 of the second outer shaft 103 may be sharpened. With such a configuration, the penetration of the anchor device 100 into the tissues becomes easier.

The anchor device 100 may be asymmetric. The length of the first end portion 114 between the end 104 and the first position 112 of the first outer shaft 102 may be different from the length of the second end portion 115 between the end 105 and the second position 113 of the second outer shaft 103. With such a configuration, one of the end 104 and the end 105 is defined as a distal end on a side that is caused to penetrate the tissues, and the other is defined as a proximal end on a side closer to the operator of the anchor device 100. Thus, one of the first end 104 and the second end 105 and the other of the first end 104 and the second end 105 can be distinguished from each other.

The first end portion 114 and the second end portion 115 may be omitted, or members having any shape other than a shaft may be used as long as the elongated anchor arms 107 and 109 can be coupled.

The elongated anchor arms 107 of the first anchor part 106 and the elongated anchor arms 109 of the second anchor part 108 may vary in size and/or number.

The lengths of the plurality of elongated anchor arms 107 of the first anchor part 106 may be different from each other, and the lengths of the plurality of elongated anchor arms 109 of the second anchor part 108 may also be different from each other.

A plurality of first anchor parts 106 may be formed along the inner shaft 101, and a plurality of second anchor parts 108 may be formed along the inner shaft 101.

The plurality of elongated anchor arms 107 of the first anchor part 106 and the plurality of elongated anchor arms 109 of the second anchor part 108 are formed by cutting out the first outer shaft 102 and the second outer shaft 103 with cutting means such as a laser processing device. However, the forming method of the plurality of elongated anchor arms 107 and 109 is not limited.

The inner shaft 101 may be solid.

Under a state in which no external pressure is applied to the outer shafts 102 and 103, each of the plurality of elongated anchor arms 107 of the first anchor part 106 and the plurality of elongated anchor arms 109 of the second anchor part 108 forms an angle of 90° at maximum with respect to the longitudinal axis of each of the outer shafts 102 and 103. However, the elongated anchor arms 107 and 109 may be configured so that the elongated anchor arms 107 and 109 each move to a position at which the θ is more than 90°, preferably a position at which the θ is from 150° to 180° with respect to the longitudinal axis of each of the outer shafts 102 and 103 when external pressure is applied to the elongated anchor arms 107 and 109 from the expanded direction to the converged direction of the elongated anchor arms 107 and 109 (that is, in a direction from the second end 105 to the first end 104 in parallel to the longitudinal axis of the outer shaft 102 with respect to the elongated anchor arms 107 in FIG. 12, and in a direction from the first end 104 to the second end 105 in parallel to the longitudinal axis of the outer shaft 103 with respect to the elongated anchor arms 109 in FIG. 12). In this case, when the anchor device 100 is expanded to fix the gallbladder wall 20 and the duodenal wall 22 to each other, and then the anchor device 100 is pulled out from the tissues and retrieved, both of the first anchor part 106 and the second anchor part 109 are expanded in a direction opposite to the direction in which the anchor device 1 is pulled out. Accordingly, the collection of the anchor device 100 becomes easier.

The application of the anchor device 100 according to the second embodiment is not limited to gallbladder-duodenal bypass surgery. For example, the anchor device 100 according to the second embodiment may be used for connecting two tissues including hollow organs other than the duodenum, such as a hollow organ and a hollow organ, a hollow organ and a parenchymal organ, a parenchymal organ and a parenchymal organ, a mesothelium and a hollow organ, and a mesothelium and a parenchymal organ, to each other.

In addition, the present invention may also adopt the following configurations.

(1) An anchor device configured to connect a plurality of tissues to each other, including: a shaft having a longitudinal axis; and a first anchor part and a second anchor part which are separated from each other and which are each formed in the shaft, wherein the first anchor part includes a plurality of elongated anchor arms that are allowed to be expanded in a direction of separating from the longitudinal axis of the shaft toward the second anchor part with a first position of the shaft being a base point, and wherein the second anchor part includes a plurality of elongated anchor arms that are allowed to be expanded in a direction of separating from the longitudinal axis of the shaft toward the first anchor part with a second position of the shaft being a base point.

(2) The anchor device according to Item (1), wherein the plurality of elongated anchor arms of the first anchor part and the plurality of elongated anchor arms of the second anchor part axe continuous parts of the shaft.

(3) The anchor device according to Item (1) or (2), wherein the plurality of elongated anchor arms of the first anchor part and the plurality of elongated anchor arms of the second anchor part are formed of portions obtained by cutting out the shaft between the first position and the second position.

(4) The anchor device according to any one of Items (1) to (3), wherein the plurality of elongated anchor arms of the first anchor part and the plurality of elongated anchor arms of the second anchor part are allowed to assume a contracted state forming an angle of from 0° to 10° with respect to the longitudinal axis of the shaft.

(5) The anchor device according to any one of Items (1) to (4), wherein the plurality of elongated anchor arms of the first anchor part and the plurality of elongated anchor arms of the second anchor part are allowed to be expanded to 45° at maximum with respect to the longitudinal axis of the shaft.

(6) The anchor device according to any one of Items (1) to (5), wherein the first position and the second position of the shaft are separated from both ends of the shaft.

(7) The anchor device according to any one of Items (1) to (6), wherein the anchor device is self-expandable.

(8) The anchor device according to Item (7), wherein, under a state in which no external pressure is applied, the plurality of elongated anchor arms of the first anchor part and the plurality of elongated anchor arms of the second anchor part each form an angle of preferably 90° at maximum, more preferably 75° at maximum, still more preferably 45° at maximum with respect to the longitudinal axis of the shaft.

(9) The anchor device according to any one of Items (1) to (8), wherein the shaft contains a metal, a metal alloy, a thermoplastic plastic, or a biodegradable resin.

(10) The anchor device according to any one of Items (1) to (9), wherein the anchor device is to be used for connecting two tissues, such as a hollow organ and a hollow organ, a hollow organ and a parenchymal organ, a parenchymal organ and a parenchymal organ, a mesothelium and a hollow organ, and a mesothelium and a parenchymal organ, to each other.

(11) A method of connecting two tissues to each other, including: (I) inserting a needle tube into a forceps channel in an ultrasonic endoscope, to thereby cause the needle tube to penetrate through the two tissues; and (II) pushing out the anchor device of any one of Items (1) to (10) from the needle tube to expand the anchor device, to thereby hold the two tissues between the first anchor part and the second anchor part.

(12) An anchor device configured to connect a plurality of tissues to each other, including: an inner shaft having a longitudinal axis; a first outer member and a second outer member which are separated from each other and which are each mounted on an outer peripheral surface of the inner shaft; and a first anchor part and a second anchor part which are formed in the first outer member and the second outer member, respectively, wherein the first anchor part includes a plurality of elongated anchor arms that are allowed to be expanded in a direction of separating from the longitudinal axis of the first outer member toward the second anchor part, and wherein the second anchor part includes a plurality of elongated anchor arms that are allowed to be expanded in a direction of separating from the longitudinal axis of the second outer member toward the first anchor part.

(13) The anchor device according to Item (12), wherein the plurality of elongated anchor arms of the first anchor part and the plurality of elongated anchor arms of the second anchor part are continuous parts of the first outer member and the second outer member, respectively.

(14) The anchor device according to Item (12) or (13), wherein the plurality of elongated anchor arms of the first anchor part and the plurality of elongated anchor arms of the second anchor part are formed of portions obtained by cutting out the first outer member and the second outer member, respectively.

(15) The anchor device according to any one of (12) to (14), wherein the plurality of elongated anchor arms of the first anchor part and the plurality of elongated anchor arms of the second anchor part are allowed to assume a contracted state forming an angle of from 0° to 10° with respect to the longitudinal axis of each of the first outer member and the second outer member.

(16) The anchor device according to any one of Items (12) to (15), wherein the plurality of elongated anchor arms of the first anchor part and the plurality of elongated anchor arms of the second anchor part are allowed to be expanded to 45° at maximum with respect to the longitudinal axis of each of the first outer member and the second outer member.

(17) The anchor device according to any one of Items (12) to (16), wherein the plurality of elongated anchor arms of the first anchor part are allowed to be expanded in a direction of separating from the longitudinal axis of the first outer member toward the second anchor part with a first position of the first outer member being a base point, wherein the plurality of elongated anchor arms of the second anchor part are allowed to be expanded in a direction of separating from the longitudinal axis of the second outer member toward the first anchor part with a second position of the second outer member being a base point, and wherein the first position of the first outer member and the second position of the second outer member are separated from a first end of the first outer member and a second end of the second outer member, respectively.

(18) The anchor device according to any one of Items (12) to (17), wherein the anchor device is self-expandable.

(19) The anchor device according to Item (18), wherein, under a state in which no external pressure is applied, the plurality of elongated anchor arms of the first anchor part and the plurality of elongated anchor arms of the second anchor part each form an angle of preferably 90° at maximum, more preferably 75° at maximum, still more preferably 45° at maximum with respect to the longitudinal axis of the shaft.

(20) The anchor device according to any one of Items (12) to (20), wherein each of the inner shaft and the outer shaft contains a metal, a metal alloy, a thermoplastic plastic, or a biodegradable resin.

(21) The anchor device according to any one of Items (12) to (20), wherein the anchor device is to be used for connecting two tissues, such as a hollow organ and a hollow organ, a hollow organ and a parenchymal organ, a parenchymal organ and a parenchymal organ, a mesothelium and a hollow organ, and a mesothelium and a parenchymal organ, to each other.

(22) A method of connecting two tissues to each other, including: (I) inserting a needle tube into a forceps channel in an ultrasonic endoscope, to thereby cause the needle tube to penetrate through the two tissues; and (II) pushing out the anchor device of any one of Items (12) to (21) from the needle tube to expand the anchor device, to thereby hold the two tissues between the first anchor part and the second anchor part.

EXAMPLES

In order to fix gastrointestinal tract walls to each other as simply and firmly as possible, the inventors have developed a shaft-like anchor device having a plurality of pinnate protrusions (anchor arms) and investigated the function of the anchor device in the body of a living porcine. The inventors propose an operative method involving reliably fixing the gallbladder wall and the gastrointestinal tract wall with the anchor device as preliminary treatment of endoscopic ultrasound-guided gallbladder drainage (EUS-GBD), to thereby significantly lower the difficulty of the EUS-GBD and the risk of accidental symptoms after treatment.

1. Object

An anchor device that can be used for preliminary treatment of the EUS-GBD was developed, and an attempt was made to cause the gastric wall and the gallbladder wall to adhere to each other in the body of a living porcine. Thus, the feasibility and safety of the anchor device for clinical application were evaluated.

2. Method

The anchor device 1 according to the embodiment illustrated in FIG. 1 was designed through use of a nickel-titanium alloy for medical use. A biopsy needle (19 gauges, inner diameter of about 0.9 mm) was assumed for indwelling, and hence a pipe material made of a nickel-titanium alloy having a diameter of 0.84 mm and a length of 20 mm was used for smooth insertion, and a structure of an arm portion was formed by laser cutting.

Next, the preliminary treatment of the EUS-GBD using the anchor device is described. First, the gallbladder is visualized from the stomach or duodenum through use of a convex EUS (GF-UCT260, Olympus Corporation), and a gallbladder wall is punctured from the stomach through use of an EUS-FNA biopsy needle (EZ Shot 3 Plus, Olympus Corporation) having a stylet removed therefrom. The anchor device is inserted from a hand side of the biopsy needle through use of a special auxiliary tool, and pushed therein up to a needle tip through use of the stylet. It is recognized on a perspective screen and an EUS screen that the anchor arm on a distal end side of the anchor device is fully expanded at the tip of the biopsy needle in the gallbladder. Then, while the tip of the EUS is pressed, the biopsy needle is slowly pulled to bring the distal end side of the anchor device into contact with the gallbladder wall. When the biopsy needle is completely pulled out, the anchor arm of the anchor device on a proximal end side is expanded. By performing the same treatment at two to three locations in total, the gallbladder wall and the gastric wall are more firmly fixed to each other.

Figure 15A:
FIG. 15A and FIG. 15B are a transparent image and a schematic view of dilatation treatment with a dilator, respectively.
Figure 15B:
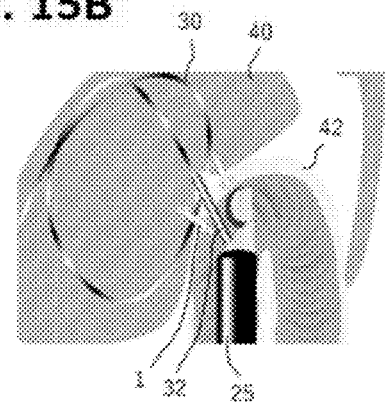

After the anchor device was indwelled, a part in which indwelling was performed was punctured with the biopsy needle again, and a guide wire (VisiGlide2, Olympus Corporation) was indwelled. After that, dilatation with a dilator (ES dilator, Zeon Medical Inc.) was performed, and a drainage tube (double pigtail tube, 7Fr, 150 mm custom-made product, Forte Grow Medical Co., Ltd.) was indwelled (FIG. 15A). Referring to FIG. 15B for description, there are illustrated the anchor device 1 (two anchor devices are illustrated), the endoscope 25, a guide wire 30, a dilator 32, a gallbladder 40, and a gastric wall 42.

An animal experiment was conducted at Tohoku University in accordance with the "Rules for Animal Experiments, etc. at Tohoku University" after being reviewed and approved by the Animal Experiment Committee. Four domesticated pigs having a weight of from 38 kg to 42 kg were used in the experiment. An attempt was made to indwell the above-mentioned anchor device in the four pigs, and the success ratio of treatment and treatment time were investigated. Two of the four pigs were bred for 17 days and 34 days, respectively, after the treatment to evaluate long-term stability and safety.

3. Results

Figure 16:
FIG. 16 is an endoscopic image after indwelling of the anchor device.

In one of the four pigs, the gallbladder was not able to be visualized from a gastric wall, and hence an attempt was made to indwell the anchor device in each of the three pigs so as to cause the gallbladder and the stomach to adhere to each other through the procedure illustrated in FIG. 5. In all the cases of the three pigs, it was possible to visually recognize from the EUS image that the anchor arm on the distal end side of the anchor device was expanded in the gallbladder (data is omitted). In addition, the gallbladder wall was pulled toward the gastric wall by pulling the biopsy needle, and thus, the anchor device was indwelled. An endoscopic image after indwelling is shown in FIG. 16. It was visually recognized that the anchor arm on the proximal end side of the anchor device was expanded and indwelled on the gastric wall. The average treatment time for the three pigs was 15.3 minutes (13 min, 15 min, and 18 min).

Figure 17:
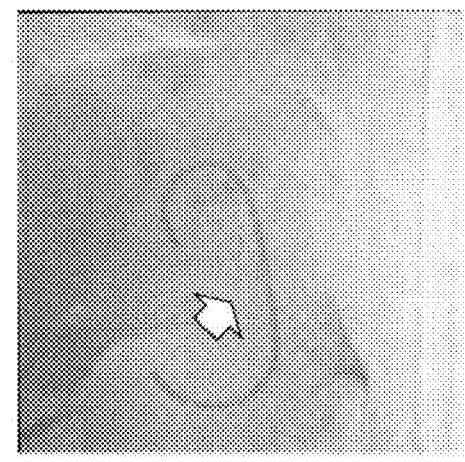
FIG. 17 is a transparent image after indwelling of a drainage tube, in which three anchor devices are observed at a position indicated by the arrow.

In one of the three pigs, a drainage tube was further indwelled, resulting in success (FIG. 17).

Next, anatomical findings are described. One pig in which the drainage tube has been inserted was dissected on the same day, and it was possible to recognize that the gallbladder wall and the gastric wall were fixed to each other with the anchor device (data is not shown). One pig that was bred for 34 days was subjected to laparotomy cholecystectomy. The gallbladder to be excised and the stomach adhered to each other in a surface of 4 cm², and the gallbladder was able to be peeled off without damaging the gallbladder wall. Meanwhile, in one pig that was dissected 17 days later, the anchor arm on the gallbladder wall side of the anchor device was damaged, and the gallbladder and the gastric wall did not adhere to each other. In one of the two pigs that were bred after the experiment, the gallbladder and the gastric wall adhered to each other with the anchor device, and the adhesion rate was 50%.

In the three cases in which the gallbladder of the pig was able to be visualized, it was recognized that the anchor device was able to be indwelled and there was no problem in expansion operation in the living body. The fact that the anchor device was able to be indwelled in the porcine gallbladder, which is more vulnerable than the human gallbladder, indicates the possibility of clinical application of the device of the present invention.

The invention claimed is:

1. An anchor device configured to connect a plurality of tissues to each other, comprising:
    an inner shaft having a longitudinal axis;
    a first outer member and a second outer member which are separated from each other and which are each mounted on an outer peripheral surface of the inner shaft; and
    a first anchor part and a second anchor part which are formed in the first outer member and the second outer member, respectively,
    wherein the first anchor part includes a plurality of elongated anchor arms that are allowed to be expanded, from a contracted state, so as to separate in a direction away from the longitudinal axis of the first outer member and pivot in a direction away from the second anchor part so as to be in an expanded state, and wherein in the expanded state, distal ends of the plurality of the elongated anchor arms of the first anchor part are spaced apart from one another in a circumferential direction of the inner shaft,
    wherein the second anchor part includes a plurality of elongated anchor arms that are allowed to be expanded, from a contracted state, so as to separate in a direction away from the longitudinal axis of the second outer member and pivot in a direction away from the first anchor part so as to be in an expanded state, and wherein in the expanded state, distal ends of the plurality of the elongated anchor arms of the second anchor part are spaced apart from one another in the circumferential direction of the inner shaft,
    wherein the first outer member and the second outer member are longitudinally fixed at opposite ends of the inner shaft, respectively, in the contracted state and the expanded state of the plurality of elongated anchor arms of each of the first anchor part and the second anchor part, and
    wherein the plurality of the elongated anchor arms of the first anchor part move to a position at which an angle that each of the plurality of elongated anchor arms of the first anchor part forms with respect to the longitudinal axis of the inner shaft is more than 90° when external pressure is applied to the elongated anchor arms of the first anchor part in a direction extending along the longitudinal axis of the inner shaft from the second anchor part to the first anchor part, or wherein the plurality of the elongated anchor arms of the second anchor part move to a position at which an angle that each of the plurality of elongated anchor arms of the second anchor part forms with respect to the longitudinal axis of the inner shaft is more than 90° when external pressure is applied to the elongated anchor arms of the second anchor part in a direction extending along the longitudinal axis of the inner shaft from the first anchor part to the second anchor part.

2. The anchor device according to claim 1, wherein, in the expanded state and in a state in which no external pressure is applied, each of the plurality of elongated anchor arms of the first anchor part and the plurality of elongated anchor arms of the second anchor part forms an angle θ of 75° at maximum with respect to the longitudinal axis of the inner shaft.

3. The anchor device according to claim 1, wherein the plurality of elongated anchor arms of the first anchor part and the plurality of elongated anchor arms of the second anchor part are continuous parts of the first outer member and the second outer member, respectively.

4. The anchor device according to claim 1, wherein the plurality of elongated anchor arms of the first anchor part and the plurality of elongated anchor arms of the second anchor part are each movable into the contracted state so as to form an angle of from 0° to 10° with respect to the longitudinal axis of the inner shaft.

5. The anchor device according to claim 1, wherein the anchor device is self-expandable.

6. The anchor device according to claim 1, wherein the first outer member and the second outer member are outer shafts.

7. The anchor device according to claim 1, wherein a plurality of the first anchor parts and a plurality of the second anchor parts are formed.

8. The anchor device according to claim 1, wherein in the expanded state, the distal ends of the plurality of elongated anchor arms of the first anchor part and the distal ends of the plurality of elongated anchor arms of the second anchor part are arranged to contact the plurality of tissues so that the plurality of tissues between the first anchor part and the second anchor part are caused to adhere to each other.

9. The anchor device according to claim 1, wherein the plurality of elongated anchor arms of the first anchor part are formed by cutting portions of the first outer member such that proximal ends of the elongated anchor arms remain continuous with the first outer member, wherein the plurality of elongated anchor arms of the second anchor part are formed by cutting portions of the second outer member such that proximal ends of the elongated anchor arms remain continuous with the second outer member.

10. The anchor device according to claim 1, wherein the position at which the angle that each of the plurality of elongated anchor arms of the first anchor part forms with respect to the longitudinal axis of the inner shaft is more than 90° is a position at which the angle that each of the plurality of elongated anchor arms of the first anchor part forms with respect to the longitudinal axis of the inner shaft is 150° to 180°, or wherein the position at which the angle that each of the plurality of elongated anchor arms of the second anchor part forms with respect to the longitudinal axis of the inner shaft is more than 90° is a position at which the angle that each of the plurality of elongated anchor arms of the second anchor part forms with respect to the longitudinal axis of the inner shaft is 150° to 180°.

* * * * *